US010445378B2

(12) United States Patent
Sasidhar

(10) Patent No.: US 10,445,378 B2
(45) Date of Patent: *Oct. 15, 2019

(54) STORING STRUCTURED AND UNSTRUCTURED CLINICAL INFORMATION FOR INFORMATION RETRIEVAL

(71) Applicant: THE CLEVELAND CLINIC FOUNDATION, Cleveland, OH (US)

(72) Inventor: Madhu Sasidhar, Pepper Pike, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 550 days.

This patent is subject to a terminal disclaimer.

(21) Appl. No.: 15/181,661

(22) Filed: Jun. 14, 2016

(65) Prior Publication Data

US 2016/0371375 A1 Dec. 22, 2016

Related U.S. Application Data

(63) Continuation of application No. 13/712,446, filed on Dec. 12, 2012, now Pat. No. 9,384,322.

(Continued)

(51) Int. Cl.
G06F 16/951 (2019.01)
G06F 16/248 (2019.01)
(Continued)

(52) U.S. Cl.
CPC .......... G06F 16/951 (2019.01); G06F 16/248 (2019.01); G06F 16/258 (2019.01);
(Continued)

(58) Field of Classification Search
CPC ............... G06F 17/30864; G06F 19/00; G06F 17/30622; G06F 17/30569;
(Continued)

(56) References Cited

U.S. PATENT DOCUMENTS 5,608,904 A 3/1997 Chaudhuri et al.
6,021,202 A 2/2000 Anderson et al.
(Continued)

FOREIGN PATENT DOCUMENTS

KR 100706765 B1 4/2007
WO 2005034213 A2 4/2005

OTHER PUBLICATIONS

PCT International Search Report for PCT/US2012/069221, filed Dec. 12, 2012, pp. 1-11.

(Continued)

Primary Examiner — Christopher L Gilligan
Assistant Examiner — C. Luke Gilligan
(74) Attorney, Agent, or Firm — Tarolli, Sundheim, Covell & Tummino LLP

(57) ABSTRACT

A computer-implemented method can include acquiring data from at least one data source, the acquired data including health data for a patient. The acquired data can be transformed into episode model data according to a context-specific data model and the episode model data can be stored in a database. The method also includes generating at least one inverted index document for at least a portion of an episode for the patient based on the episode model data.

20 Claims, 10 Drawing Sheets

Related U.S. Application Data

(60) Provisional application No. 61/569,579, filed on Dec. 12, 2011.

(51) Int. Cl.
  *G16H 10/60* (2018.01)
  *G06F 16/25* (2019.01)
  *G06F 16/28* (2019.01)
  *G06F 16/31* (2019.01)
  *G06F 16/9535* (2019.01)
  *G16H 40/63* (2018.01)

(52) U.S. Cl.
  CPC .......... *G06F 16/285* (2019.01); *G06F 16/319* (2019.01); *G06F 16/9535* (2019.01); *G16H 10/60* (2018.01); *G16H 40/63* (2018.01)

(58) Field of Classification Search
  CPC ......... G06F 17/30554; G06F 17/30598; G06F 17/30867; G16H 10/60; G16H 40/63
  See application file for complete search history.

(56) References Cited

U.S. PATENT DOCUMENTS

| | | |
|---|---|---|
| 6,466,942 B1 | 10/2002 | Tolkin |
| 6,915,254 B1 | 7/2005 | Heinze et al. |
| 7,225,183 B2 | 5/2007 | Gardner |
| 7,297,108 B2 | 11/2007 | Iliff |
| 7,567,957 B2 | 7/2009 | Ferrari et al. |
| 7,644,091 B1 | 1/2010 | Zubizarreta |
| 7,693,857 B2 | 4/2010 | Dettinger et al. |
| 7,769,600 B2 | 8/2010 | Iliff |
| 2004/0267722 A1 | 12/2004 | Larimore et al. |
| 2005/0071194 A1 | 3/2005 | Bormann et al. |
| 2005/0102170 A1 | 5/2005 | Lefever |
| 2007/0073668 A1* | 3/2007 | Stephan ............ G06F 17/30622 |
| 2007/0088695 A1 | 4/2007 | Bleyendaal et al. |
| 2007/0112586 A1 | 5/2007 | Dettinger |
| 2007/0260492 A1 | 11/2007 | Feied et al. |
| 2009/0063470 A1* | 3/2009 | Peled .................. G06F 17/278 |
| 2009/0076855 A1 | 3/2009 | McCord |
| 2009/0198517 A1 | 8/2009 | Ruben et al. |
| 2010/0131482 A1 | 5/2010 | Linthicum et al. |
| 2010/0169338 A1 | 7/2010 | Kenedy et al. |
| 2010/0228724 A1* | 9/2010 | Petri ................. G06F 17/30489 707/722 |
| 2011/0004588 A1 | 1/2011 | Leitersdorf et al. |
| 2011/0218821 A1* | 9/2011 | Walton .................. G06Q 50/22 705/3 |
| 2012/0066197 A1* | 3/2012 | Rana ................ G06F 17/30011 707/706 |

OTHER PUBLICATIONS

Murff, et al., Automated Identification of Postoperative . . . JAMA, Aug. 24/31, 2011, vol. 306, No. 8, pp. 848-855.

JHA. The Promise of Electronic Records . . . , JAMA, Aug. 24/31, 2011, vol. 306, No. 8, pp. 880-881.

Extended European Search Report for corresponding EP App. No. 12857036.3, dated Dec. 14, 2016, pp. 1-8.

* cited by examiner

STORING STRUCTURED AND UNSTRUCTURED CLINICAL INFORMATION FOR INFORMATION RETRIEVAL

CROSS-REFERENCE TO RELATED APPLICATION

This application claims the benefit of U.S. Provisional Patent Application No. 61/569,579 filed Dec. 12, 2011, and entitled STORING STRUCTURED AND UNSTRUCTURED CLINICAL INFORMATION FOR INFORMATION RETRIEVAL, the entire contents of which application, including appendices thereof, is incorporated herein by reference.

TECHNICAL FIELD

This disclosure relates to information retrieval systems and, more particularly to systems and methods for storing structured and unstructured clinical information, such that retrieval of such information can be facilitated.

BACKGROUND

Databases have many limitations when processing clinical information. For instance, with respect to performance, current systems cannot be scaled out for complex queries. Nested searches are difficult to perform where SQL queries, for example, are difficult, slow, and/or not possible to perform. This is due largely to the way in which existing system store clinical information in relational or column store databases. These databases are suited for read and write access to data but not for searching.

SUMMARY

This disclosure relates to systems and methods for storing structured and unstructured information to facilitate information retrieval.

As one example, a computer-implemented method can include acquiring data from at least one data source, the acquired data including health data for a patient. The acquired data can be transformed into episode model data according to a context-specific data model and the episode model data can be stored in a database. The method also includes generating at least one inverted index document for at least a portion of an episode for the patient based on the episode model data. As a result, searching (e.g., manually and/or automated) of data during the patient episode can be facilitated.

As another example, a non-transitory machine readable medium can include instructions executable by a processing resource. In such example, the instructions can include a data converter programmed to access data from at least one data source and transform the accessed data to episode data for a given patient based on a data model that defines at least one of structure and content for storing the episode data in a database for an episode of care for the given patient. An index generator can be programmed to generate an inverted index document based on the episode data. The index generator can assign a name to classify selected data objects of the episode data within the episode of care.

DETAILED DESCRIPTION

This disclosure relates to a system and method for storing structured and unstructured clinical information for information retrieval. Data from one or more sources can be converted to a desired structure according to context-specific data model (e.g., for a clinical context). In some examples, the data model can define a temporal segmentation of data for a health care episode and classifying data elements to provide converted episode data for one or more patients. An index generator can process the converted episode data and generate at least one inverted index document for one or more patients. For instance, multiple inverted index documents can be generated for a given patient episode.

Each inverted index document stores data in a clinically useful format that facilitates querying, such by a user via a search engine, by automated methods or a combination thereof. Specialized ranking algorithms can be employed allow the user to control ranking of the result set. Automated clustering algorithms can be employed during the search. This includes obtaining datasets for clinical research and using crafted queries for "clinical intelligence" applications to improve outcome and achieve regulatory compliance. Free text searching can be provided along with search result scoring to facilitate ranking of information. Automated result clustering can also be provided utilizing data mining algorithms, for example.

Figure 1:
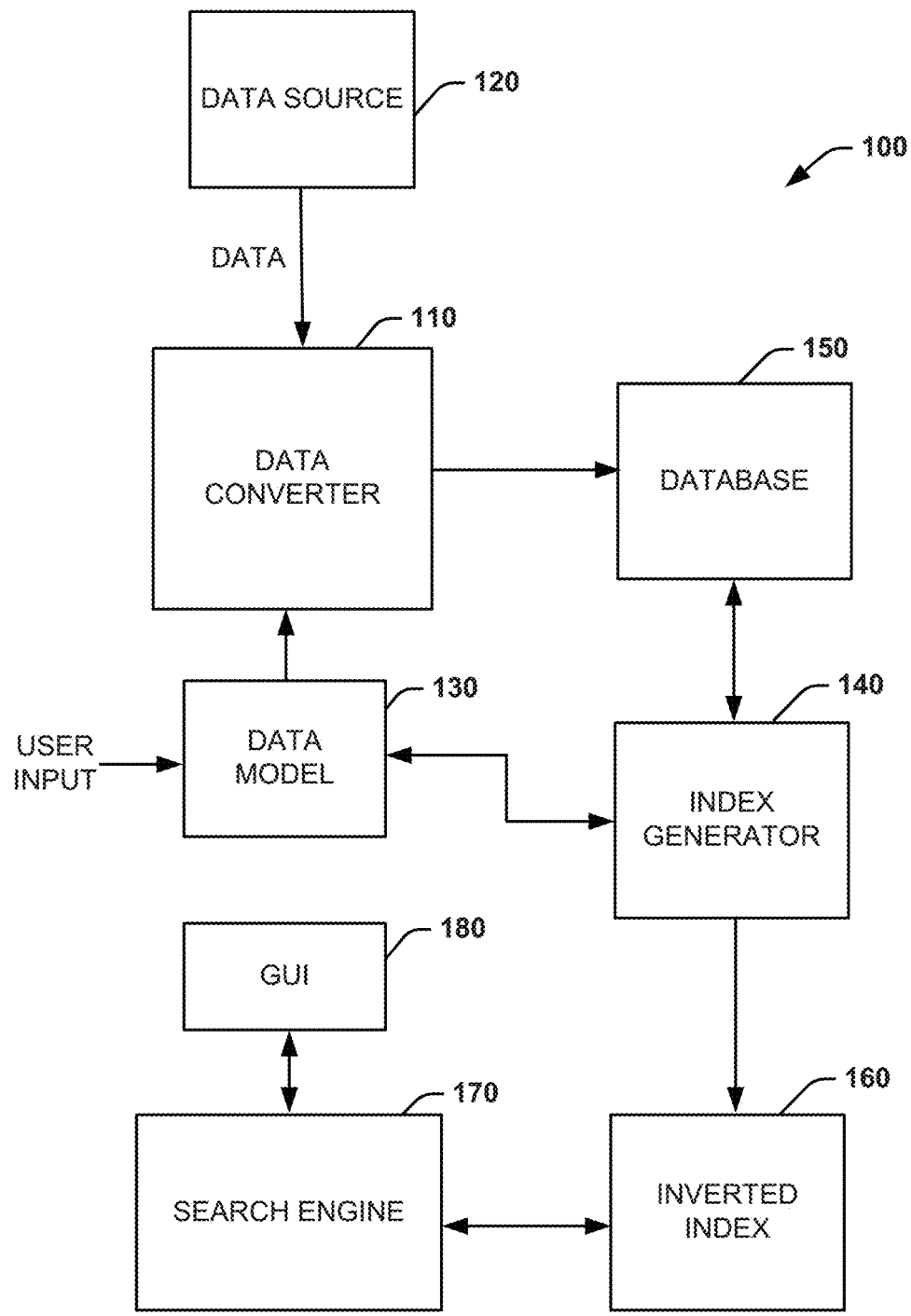
FIG. 1 illustrates an example of a system for storing structured and unstructured clinical information.

FIG. 1 illustrates an example of a system 100 for storing structured and unstructured clinical information. A data converter 110 can be configured to process data stored in one or more data source 120. The data converter 110 can be implemented as instructions stored in a non-transitory machine-readable medium, such as can be accessed and executed by a processing resource (e.g., one or more processor core). For example, the data source 120 can be an electronic medical record (EMR) repository of a health care enterprise. Other examples of data sources can include a laboratory information system, predictive analytics system, admission-discharge transfer systems or other sources of information. The information can be a compilation from any number of one or more sources of data, such as can be distributed across one or more health care enterprises or other data sources. Such data sources 120 can be co-located in a computing machine or be distributed across a computer network (e.g., a local area network or wide area network). The information in the data source 120 can also store information derived from an electronic medical record of patients, such as healthcare analytics.

The data converter 110 can be programmed to convert data from the data source 120 to a converted set of data according to a predetermined data model 130. The converted data can be stored in a database 150. The database 150 can be stored in non-transitory memory. Such memory could be implemented, for example, as volatile memory (e.g., random access memory), nonvolatile memory (a hard disk drive, a solid state drive, flash memory or the like) or a combination thereof. In some examples, the database 150 can be implemented as a relational database 150 that stores the converted data in a set of formally described tables organized based on the data model 130.

In some examples, the data converter 110 can be programmed to obtain data selectively from the source 120 such as for one or more given patient episodes. As used herein, the term "episode" refers to a sequence of services. Thus a patient episode can encompass a sequence of health care services for a given patient, such as can include treatment, monitoring and observation, procedures, tests, as well as who or what provides such services, where the patient is during such services and when such services are provided. The episode thus can include any combination of inpatient care, outpatient care, laboratory tests, imaging and the like related to one or more patient conditions for which treatment is being sought. The episode can also involve one or more different healthcare providers, in which case the data sources 120 may be maintained separately.

The data model 130 can impose a standard format on to the data within the relational database to facilitate processing by an index generator 140. The particular format of the data model can vary depending the type of patient episode. For instance, a different model may be utilized for an episode involving inpatient care in an intensive care unit than the model use for an episode involving an outpatient surgical procedure. Thus, a plurality of data models can be provided and configured for a variety of different purposes, such as in response to a user input.

As mentioned above, the database 150 can be a relational database 150 to store the instance of converted episode data according to a schema defined by the data model 130. In one example, the data model 130 defines a structure and arrangement of selected episode data that is storable in the relational database 150 for subsequent interpretation via the index generator 140. The data converter 110 can also be programmed based on the data model 130 to calculate one or more data values based on the episode data from the data source 120. One example, of a computed data value that the converter can generate and store in the database 150 is an indication of a length of stay for the patient. Other values could be computed (e.g., analytics) by the data converter 110 and stored in the database 150 for the episode. Other information associated with the data model 130 can be stored in the database 150, such as can include a separate header indicating patient names and identification numbers, for example.

As a further example, the data converter 110 can be configured to categorize each data object in the episode data according to a predetermined schema for generating the inverted index. As an example, the data converter 110 can insert a field classifier into each field that is to be expressed in the inverted index 160 based on the predefined data model 130. In some examples, the data converter 110 prepends episode data fields with at least three fields that include a prefix, a field name, and a suffix. The data converter 110 thus can provide such fields to each data object (e.g., data field) in the episode record based on the requirements of the model 130.

By way of further example, the prefix can be a temporal parameter for each data object in the acquired episode data. For example, the data converter 110 can segment the episode data into a plurality of time segments based on timing data in the record. The designation and length of the time segments can be specified by the model 130. For instance, each time segment can include a time range time relative to a time for a specified event (e.g., predefined or user-specified). In some examples, the event can be a time for when the inverted index is generated. Other events and times can be used, such as can be the time of patient admission, patient discharge or the like. This as well as other parameters of the model can be programmable in response to a user input. The data converter 110 can add a corresponding prefix to each data object (e.g., a data field) according to in which of the plurality of time segments the respective data object has been determined to reside.

The field name can include one or more words or acronyms or abbreviations that describe each data field in the database 150. For example, the name field could include the name of the unit where the patient was checked in (e.g., ICU, maternity, and so forth) or could include the name of a test or lab, for example. The suffix can specify a type of data in each respective field. The suffix field can indicate a particular characteristic or quality about the data, which can vary depending on the type of data (e.g., is it a text value, a numeric value such as an integer or floating point number).

The index generator 140 can access the converted episode data in the database 150 to generate an inverted index 160. The index generator 140 can be implemented as instructions stored in a non-transitory machine-readable medium, such as can be accessed and executed by a processing resource (e.g., one or more processor cores). In some examples, the inverted index 160 can be provided in the form of a document containing searchable terms of clinical information derived from the data source 120 and characterized according to the data model 130. The index generator 140 can build the index 160 according to various strategies, which can be dependent on the clinical context and purpose in which the system 100 is being utilized.

As used herein, a data field is a named section of the inverted index document that includes two parts: a name part and a value part. Thus each document that is generated includes a set of data fields based on the ingested data and according to constraints and requirements of the data model. The name for each data field in the document includes a fully qualified name that includes a prefix (e.g., indicating an associated time segment), a field name, and an indication of the type for the value part of the data field. As mentioned above, the field types specified in the element names can include text, numeric (e.g., integer, floating point) and dates. Numeric and date value parts are special types of fields with mechanisms that allow range queries by a search engine 170.

The index generator 140 can also employ semantic expansion of certain data fields to provide semantically expanded versions of such data fields, which can be utilized in the inverted index document. For example, the index generator 140 can employ a library or other semantic tool or library to semantically expand text or other data fields in the model data to include known synonyms or other equivalents for such terms in the inverted index 160. In this way, terms stored as data fields (e.g., value parts of the data field) can encompass a standard or user-defined vocabulary, such as to facilitate corresponding searching of terms.

As a further example, the database 150 and resulting inverted index 160 can be generated at a desired interval, such as can be periodically (e.g., hourly or daily) or intermittently at times of light usage for the data source 120. For instance, a scheduling application (not shown) can be programmed to provide a corresponding trigger to the system for a selected cohort of patients, such as can include all patients with active encounters or different subsets of patients. The data model 130 utilized for each subset can be the same or different, such as disclosed herein. In other examples, the database 150 and inverted index can be generated in response to a user input requesting its trigger. In the context of a hospital or other healthcare enterprise, the database converter 110 can acquire data for each patient not discharged as well as patient's that have been discharged since the last construction.

Additionally, the index generator 140 can employ protected words and/or stop words for each respective data field. For instance, the protected words and stop words can be specified in files, such as can be user-defined terms or default terms for a given purpose. Thus, the index generator 140 can employ the files to ensure that protected terms are not removed and that stop words are tagged or removed from the inverted index that is generated. Data cleansing can also be performed to help ensure that units are standardized and data types are valid for respective fields.

A search engine 170 can be programmed to query the inverted index 160 and generate a results set. In some examples, the results set can include a ranked list of results for the clinical information based on the query. For example, the search results can be scored such as based on term frequency or inverse frequency of search terms in a query. Weighting can also be applied to search terms such as to control the order in which the search results are ranked. A graphical user interface (GUI) 180 can be provided to drive the search engine 170 (e.g. indicate what fields to search what terms to search, what (if any) weighting to apply to different search terms). Since the inverted index is stored as document it facilitates rapid searching by the search engine 170 for clinical information when compared to traditional database searching. Additionally, since each document is generated for one or more time segments of an episode, searching within such time interval is also facilitated across documents.

As a further example, in some cases, data may be padded (e.g., via the addition of leading or trailing spaces or other characters being added to data values in an instance of the data model) on either side of an entry in the inverted index 160 in order to facilitate efficient searching. For example, if a user were to qualify a search as does "not" have pneumonia, such padding can be utilized to isolate relevant terms in the inverted index 160 and to mitigate capturing/searching for data that does not pertain to the search query at hand. The inverted index 160 can be generated as an index data structure storing a mapping from content (e.g., converted EMR instances in the data model), such as words or numbers, to its locations in a database file, or in a document or a set of documents. Thus, one aspect of the inverted index 160 is to enable fast, full-text searches of clinical information by the search engine 170.

In some examples, a user can utilize the search engine 170 via the GUI 180 as demonstrated in the example of FIG. 1. Alternatively or additionally, the search engine 170 and/or the inverted index 160 can be accessed by one or more other applications (e.g., business intelligence applications). For example, the system 100 can be implemented as part of a clinical intelligence platform that can rapidly process clinical information, such as to improve clinical outcomes, generate alerts, assess regulatory compliance as well as other quantifiable metrics, facilitate research, improve coding and documentation of care as well as improve resource utilization. As a further example, the search engine can be employed by an alert generator that is programmed to execute one or more queries periodically at predetermined time intervals or in response to an event trigger. The alert generator can employ one or more rules to evaluate the search results and generate an alert (e.g., send a message via email, page, text message or the like) to one or more predefined individuals based on the evaluation indicating the occurrence of an alert condition. In other examples, the results of searching or alert conditions can be stored in the data source such as part of a given patient's record (e.g., an EMR). In some examples, the results that are stored back to the data source can also include a computed score and/or another interpretation of the search results such as can be an automated (e.g., normalization process) or in response to a user input. Since the inverted index documents are generated for a given time segment, the scoring that is performed remains relevant across documents.

Figure 2:
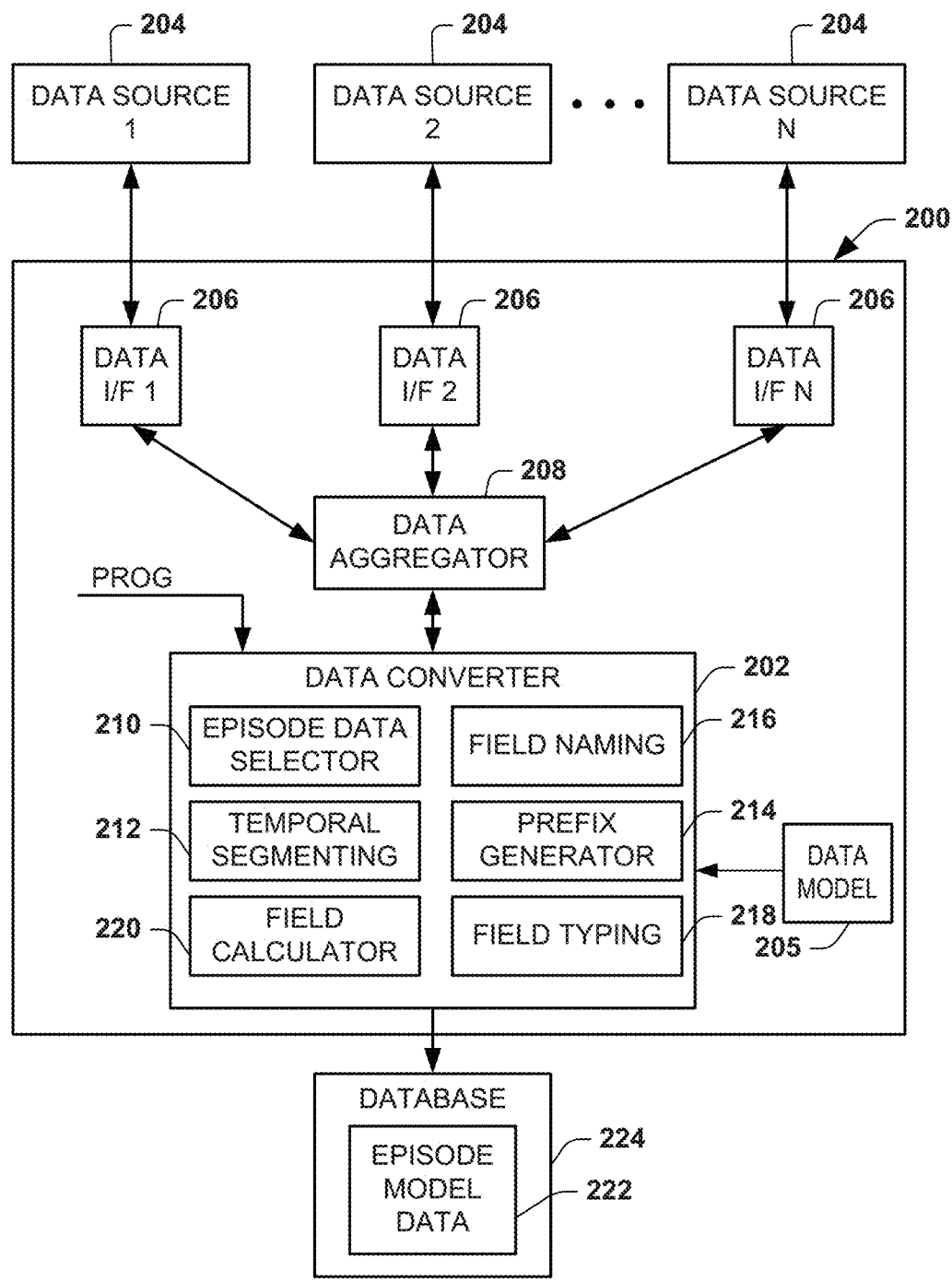
FIG. 2 illustrates an example of a system to perform data aggregation and transformation.

FIG. 2 depicts an example of a system 200 to transform data to a predetermined form that facilitates generating an inverted index. The system 200 and its components can be implemented as machine readable instructions stored in memory and executable by a processor. The system 200 includes a data converter 202 that is configured to convert data from one or more data sources 204 to the predetermined format according to a data model 205. The data converter 202 can be implemented as the data converter 110 in the example system 100 of FIG. 1. There can be any number of data sources 204, demonstrated as data source 1, data source 2 through data source N, where N is a positive integer denoting the number of sources. As disclosed herein, the data sources 204 can include one or more EMR repositories, laboratory information systems, analytic systems or the like that can provide raw data or computed data derived from the one or more of the other data sources. For instance, one of the data sources can be an EMR and another source can be a predictive analytics system programmed to employ a predictive model or inference engine to compute a likelihood of an outcome (e.g., a predicted length of stay, a predicted likelihood of developing infection or the like).

The system 200 can include a data interface 206 that is programmed to communicate with each respective data source 204, such as to access the source to retrieve or send data. Thus, in this example, the number of data interfaces matches the number of N sources. Data interfaces 206 can be added and/or removed according to the application requirements and how the methods used to store data that is used. A data aggregator 208 can collect the data from one or more of the data sources 204 via the interfaces 206. The data can be selectively accessed from the data sources based on data access parameters established per the clinical context and requirements of the associated model 205. For example, each of the data sources can be implemented as databases and the data interfaces can submit queries for data associated with one or more patients (e.g., based on patient name or other patient identifier) over a selected date range. The data aggregator can collect the data acquired from the sources and provide it to the data converter 202 for further processing based on the data model 205.

The data converter 202 can include a data selector 210 that is programmed to select episode data in the aggregate data provided by the data aggregator 208. Alternatively or additionally, the data selector 210 can set constraints for the data requests (e.g., queries) that are sent to the respective data sources 204 for obtaining the episode data. The constraints can include data identifying one or more patients (or criteria that defines a patient population), the type of data to retrieve from the data sources and a time range for such data. If known a priori, the data selector 210 can also identify the data sources 206 from which the data is to be obtained.

A temporal segmenting function 212 can segment (e.g., partition) data fields in the aggregate data according to temporal information associated with such data. The temporal duration for each segment can be defined by temporal parameters of the data model 205. The temporal duration can be fixed (e.g., 12 or 24 hour time periods) or it can be variable (e.g., a fraction of the total episode duration). Additionally or alternatively, each of the time segments could have the same duration or different segments could extend different time periods. The temporal segmenting function 212 can also create the segments relative to a predefined event as set out in the data model. For example, the event can be related to the data conversion and index generation process, a health condition of the patient, or to provider work schedules.

The data converter 202 also includes a prefix generator 214 to insert a temporal qualifier for data objects in the database. The temporal identifier can specify a temporal segment for each data object based timing information associated with the respective data object. For example, the timing information can be the time when a test, measurement, treatment or other procedure was performed on the patient. As an example where the temporal segments are 24 hour periods from creation of the index, if one test was performed 13 hours before creation (i.e., it is between time t=0 and 24 hours from creation), the prefix generator 214 can insert a temporal prefix (e.g., "d1" to indicate with a first day—24 hour time period) to the data field. Another test that was performed 26 hours before index creation can be assigned a different temporal prefix (e.g., "d2" to indicate with a second day—between 24 and 48 hours from the event) period along with all other data temporally residing within the second 24 hour period from index creation. The prefix generator 214 can perform this process for any number of temporal segments according to the data model.

As one example, the segments can include a first 24 hour period from index creation (e.g., day 1), a second period between 24 and 48 hours of index creation (e.g., day 2), a third period between 48 and 72 hours of index creation (e.g., day 3), a 24 hour period from a time of patient admission and another variable time period between 24 hours from admission and 72 hours from index creation. The set of time segments collectively can cover the entire episode such as from admission to a time when the index is generated.

A field naming component 216 is programmed to add a descriptor (e.g., a name) to data fields based the data model 205. For instance, the field naming component can determine a name for a respective data field based on the content of the field and on the naming conventions provided by the model. A fielding typing component 218 can also insert an indication of the type of the field to the data fields based on the data model 205. For example, the field typing component can analyze the data field to determine how the content is represented and based on such determination specify a type for such data. Examples of different types of data include text, integer, floating point and the like. By specifying the data type searching of a resulting inverse index can be facilitated.

The data converter 202 can also include a field calculator 220 programmed to compute or derive information from the data obtained from the data sources 204. The computed or derived information can be provided as part of the episode model data 222 provided by the data converter 202. As an example, the data model for a given clinical context can specify one The data converter 202 transforms the data from the data sources into corresponding episode model data 222 that can be stored in a database (e.g., a relational database) 224. The resulting data 222 thus can be provided in a format and with metadata (e.g., temporal prefix, field name, field type) being concatenated to provide a fully qualified name each data field based on the data model 205. In this way, pertinent data from one or more sources 204 can be transformed into a format that facilitates generation of an inverted index document as disclosed herein.

Figure 3:
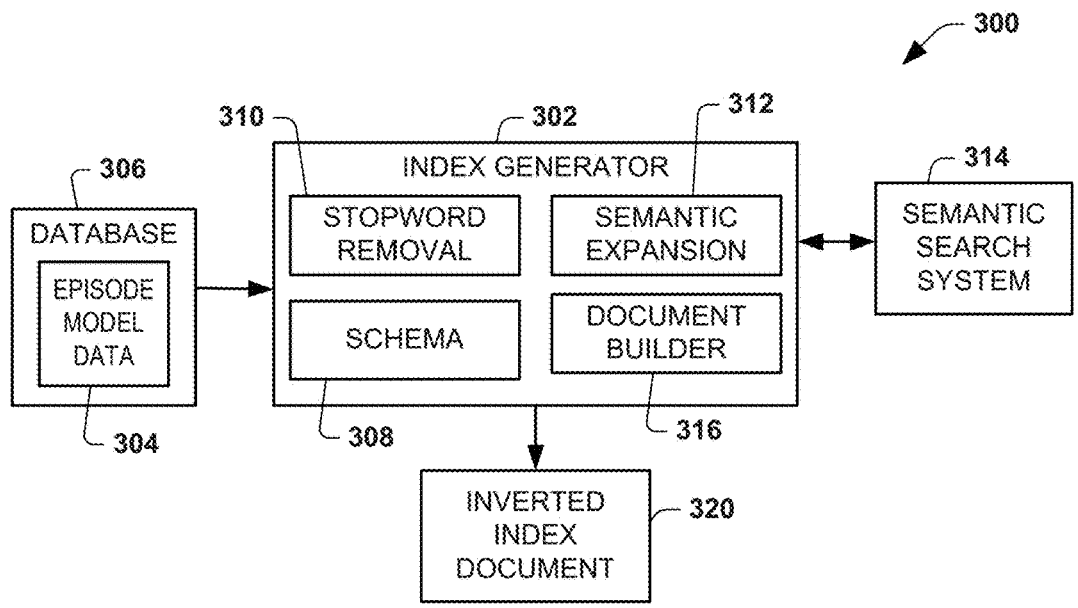
FIG. 3 illustrates an example of a system to generate an inverted index document.

FIG. 3 depicts an example of a system 300 to generate an inverted index document 320. The system 300 includes an index generator 302 such as can be implemented as the index generator 140 in FIG. 1. The index generator 302 can be implemented as machine readable instructions stored in memory and executable by a processor. The index generator 302 parses the model data 304 to construct the inverted index document 320 to facilitate searching. The model data 304 can be stored in a database (e.g., a relational database) 306. The index generator 302 is programmed generate the inverted index document 320 for each given patient episode based on model data (e.g., the episode model data 222 provided by the data converter 202 of FIG. 2) 304. In this way, any number of documents 316 can be generated and be rapidly searched via a corresponding inverted index that is provided for such documents according to a predefined schema 308.

In the example of FIG. 3, the index generator 302 employs a stop word removal function 310 to filter out (e.g., remove) a predetermined set of terms from the model data 304. The particular set of terms to be removed can vary depending on the context in which the system used and can be programmable.

The index generator 302 can also include a semantic expansion function 312 so that text data objects can cover alternate names. The semantic expansion function 312 thus can insert one or more synonym term for each term and/or phrase that is in text data object of the model data 304 such that queries for any included alternate term or phrase will result in match. In some examples, the semantic expansion function 312 can itself be programmed with a list of synonyms that can be added to the data object in the document 320. Alternatively or additionally the semantic expansion function 312 can itself be programmed to query another semantic search system 314 for a list of alternate terms or phrases for each text data object, which can include synonyms, abbreviations, codes (e.g., ICD-9, ICD-10, procedure codes or the like). The semantic search system 314, for example, can be a private or public database designed to return a list of synonyms in response to a query that includes a text data object, such as from the index generator 302.

A document builder thus can employ the resulting data to construct the inverted index document 320 according to the prescribed schema 308. Thus, the inverted index document can have stop words removed and include synonyms for remaining text objects from the model data. Additionally, each data object will include the prefix, field name and field type for such object according to the applied data model. The result is a document that can includes data that is organized according to the schema as to facilitate searching as disclosed herein. The index generator 302 can also periodically generate one or more other index, such as according to a predefined schedule according to the duration of segments or other predetermined time period. The inverted index documents 320 can be stored in a database in memory. As disclosed herein, any number of inverted index documents can be generated for any number of patients and stored in memory for being searched. Additionally results from such searching can also be stored back into a patient record (e.g., an EMR repository) via an interface (e.g., interface 206 of FIG. 2) and thereby become part of episode data that can be utilized subsequently to generate another inverted index document.

Figure 4:
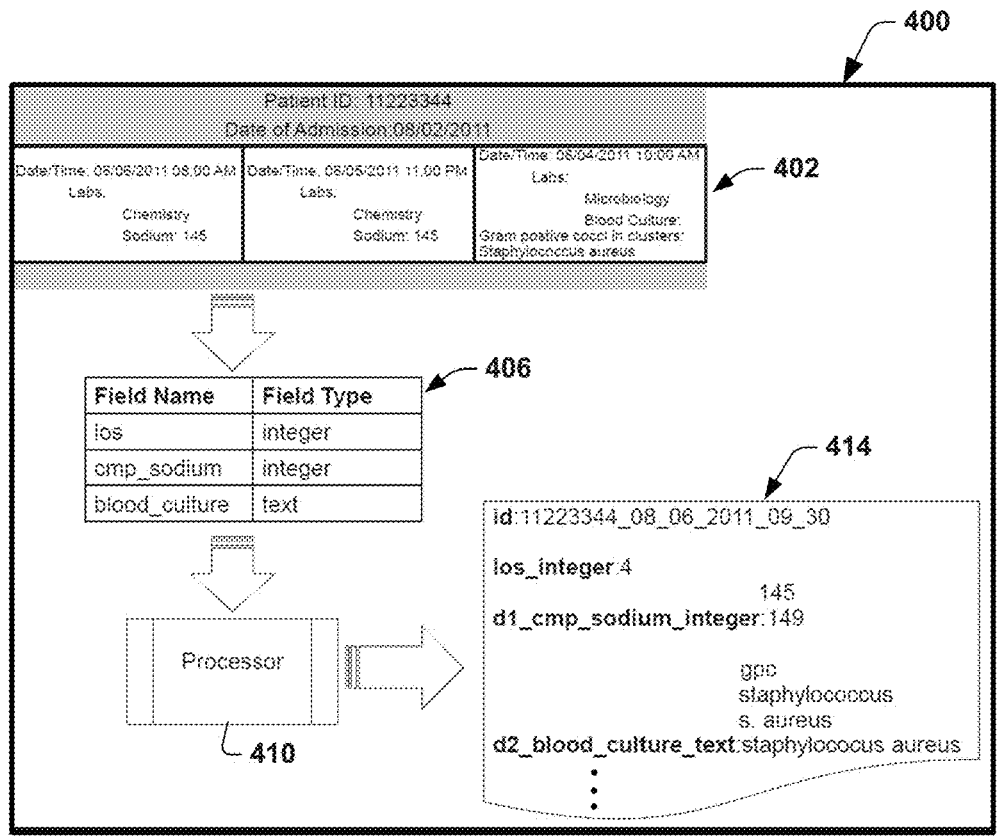
FIG. 4 illustrates an example data flow and processing for generating an inverted index document.

As a further example, FIG. 4 demonstrates a data workflow 400 for a sample set of clinical patient data 402 within a common patient episode. The patient data 402 can include data obtained from an EMR or other data source for the patient episode. In this example, the data includes data for a given patient (e.g., patient having patient ID 11223344) that was admitted on Aug. 2, 2011. The patient data 402 includes three data objects: a lab at 8:00 AM on Aug. 6, 2011; a lab at 11:00 PM on Aug. 5, 2011; and another lab at 10:00 AM on Aug. 4, 2011. The patient data can be processed by a processor 410 (e.g., executing instructions corresponding to a data converter) be transformed into model data according to the data model 406. The model data can include data that exists in the patient data record 402 as well as data derived (e.g., computed) from the patient record data. The transformed model data 406 can be stored in a database such as disclosed herein.

The processor 410 can also execute instructions (e.g., corresponding to an index generator) to generate an inverted index document 414 for the given patient episode. In this simplified example, the document 414 can include a document ID derived from the patient ID and a time reference for the document. The time reference can be the time when the document is generated, for example. As disclosed herein this can be employed as a start time or event with respect to which all other data objects are related temporally, such as into a plurality of discrete segments relative to such time base. A length of stay (LOS) data field shows the length of stay for the patient calculated (e.g., by the data converter) based on the difference between admission and the index creation time, for example.

As the data is ingested by processor 410, the date and time value for each test is compared with current date and time (e.g., at index creation) to determine the prefix. For example, the lab data values for each of the sodium tests performed on Aug. 5, 2011 and on Aug. 4, 2011 are stored in a common identifier since the both occur in the same time segment (e.g., day 1—"d1") and were the same test, which is named CMP_SODIUM (e.g., by the field naming component 216 of FIG. 2). The lab test on Aug. 4, 2011 is determined (e.g., by the prefix generator 214 of FIG. 2) to occur on day 2 and includes a text type of data field. Accordingly, the index generator can perform a semantic expansion of the text data field ("gram positive cocci in clusters" and "*Staphylococcus aureus*") to provide synonyms including "gpc", "*S. aureus*" and "*Staphylococcus*" as to facilitate searching for the original text data and semantic equivalents thereof. Thus, a given data field in the inverted index document 414 can include multiple values for a given time segment, which can include plural instances of different data values, semantic equivalents of text data and combinations thereof. By concatenating the 3 parts (e.g., the prefix, field name and field type), a fully qualified name is derived for each data field.

In this way, a unique document (similar to document 414) can be generated for each date (or other user-programmable time segment) within a given patient episode. As a result, a plurality of documents can be generated for each patient, each subsequent document covering a next segment in the episode. Since each document is generated according to the same data model, for example, D1 in a previous document will be represented as D2 in a next document that is generated, and so forth. The documents can be generated in periodically in a sequential order or, in other examples, documents can be generated substantially currently in response to a user input. Additionally, documents can be generated for all patients or a selected subset of patients, for example. As disclosed herein, the resulting documents facilitate searching.

Figure 5:
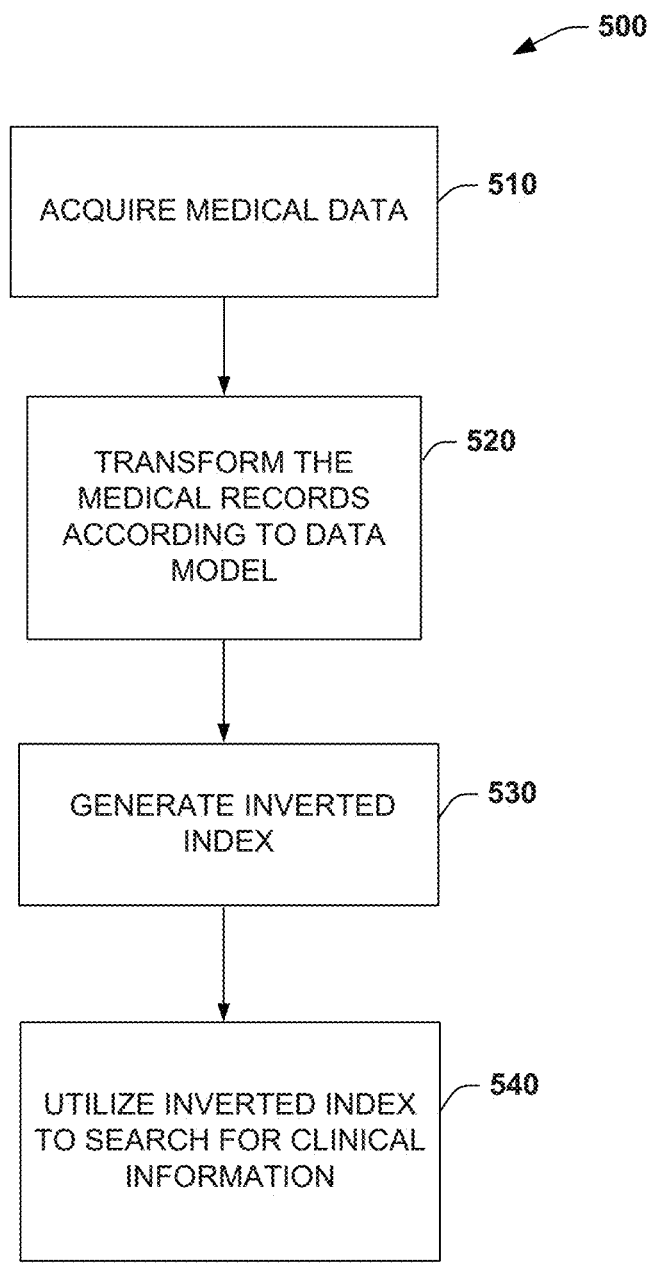
FIG. 5 illustrates an example of a method for storing structured and unstructured clinical information.

In view of the foregoing structural and functional features described above, an example method will be better appreciated with reference to FIG. 5. While, for purposes of simplicity of explanation, the method is shown and described as executing serially, it is to be understood and appreciated that the method is not limited by the illustrated order, as parts of the method could occur in different orders and/or concurrently from that shown and described herein. Such method can be implemented as instructions executed by a processor, such as in a server or other computer, for example.

FIG. 5 illustrates an example of a method 500 for storing structured and unstructured information, such as medical information. At 510, the method 500 includes acquiring medical information from a repository (e.g., data from an EMR repository and/or other data sources). The acquisition can be performed intermittently or at predetermined intervals (e.g., imported via data converter 110 of FIG. 1 or converter 202 of FIG. 2). Such data can be ingested from one or more data sources, as disclosed herein.

At 520, the method 500 includes constructing a database of the data acquired to a predetermined form (e.g., a relational database) according to a predefined data model (e.g., the data model 130 of FIG. 1, or model 205 of FIG. 2). The model can be programmed to characterize the information being acquired to facilitate searching, such as can depend on a selected clinical context and/or business objective to be achieved by such searching. For example independent documents can be generated for each patient for selected time intervals, such as beginning from an admission time (e.g., individual documents for each 24 hour period beginning from admission time). The data model can impose predetermined temporal constraints on the data to facilitate searching in a clinical context, such as disclosed herein. For example, the data can be segmented into temporal intervals which can be added to data fields (e.g., by prefix generator 214 of FIG. 2). Other classification data can also be added to data fields, such as a field name and an indication of the type of data in each field in the database, also according to the data model, which provides qualified names for each data element to further improve searching.

Additionally, at 530 the method can include utilizing the data model to generate an inverted index document that includes fully qualified searchable terms. For example, the inverted index can specify numerical as well as textual field types according a schema specified by the data model, such as disclosed herein. The index generation further can include semantic expansion of data values as well as removal of stop words. The method 500 can be employed to generate any number of documents for each of a plurality of different time segments of a given patient episode—for any number of patient episodes.

At 540, the method 500 can also include utilizing the inverted index to enable a search of clinical information through any number of inverted index documents generated according to the method for a common data model, such as for a given clinical context. The searching can be implemented via a GUI that provides access to a set of search terms that can include any terms used in the qualified names provided by the data model. As disclosed herein, in some examples, the qualified names can a prefix, a field name, and a suffix. The GUI thus can be employed to enter search terms that initiate the search for clinical information. For example, a user can select one or more search terms, such as including a time segment (e.g., corresponding to a prefix) and a field name, and specify a value or range of values for searching depending on the field type. A results set in response to querying the inverted index document can be returned to the user via the GUI.

The search at 540 can include scoring results from the search according to a number of terms that are detected in the inverted index. Additionally, or alternatively, other criteria can be used for scoring search results. This can also include ranking of the retrieved information based on a weight applied to search terms. The weighting can be set in a predefined search or, in other examples, weighting of search terms can be set in response to a user input.

Figure 6:
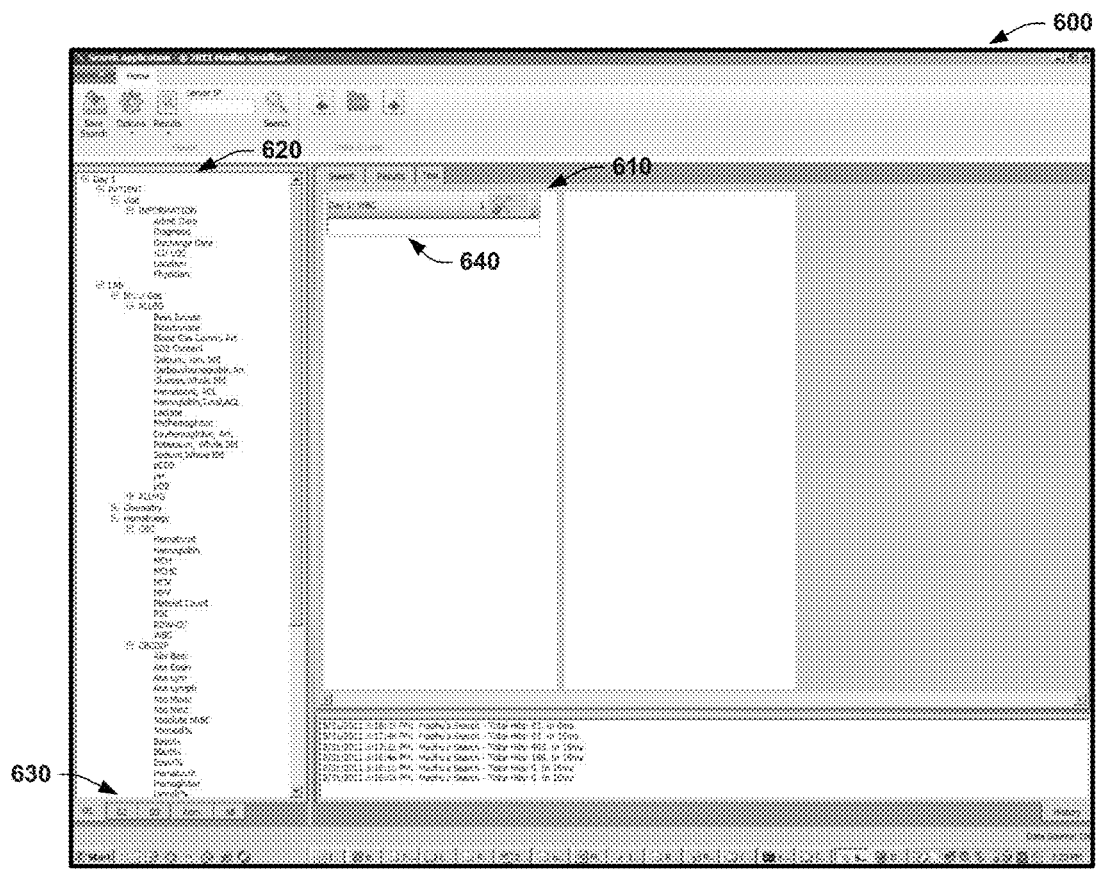
FIG. 6 illustrates an example of a graphical user interface that can implement searching.

FIGS. 6-11 provide examples of GUIs that can be implemented for storing/retrieving structured and unstructured clinical information. An example GUI 600 in FIG. 6 shows a single search palette 610 for entering search criteria. Differing search categories can be selected from a list depicted at 620. For example, each of the categories can correspond to available search terms provided according to the model utilized to generate documents being searched. At the bottom of the list 620, the GUI provides GUI elements 630 for selecting one or more available time segments (e.g., D1, D2, D3, Admission, or all) for the respective searches and selected categories. An input dialog box 640 can be provided to enter relevant search terms for the particular category selected. For a valid search the type of information that can be entered will be of the type for the selected search term (field name). In the example of FIG. 6, the search term is a white blood cell (WBC) value for a given time segment (D1).

Figure 7:
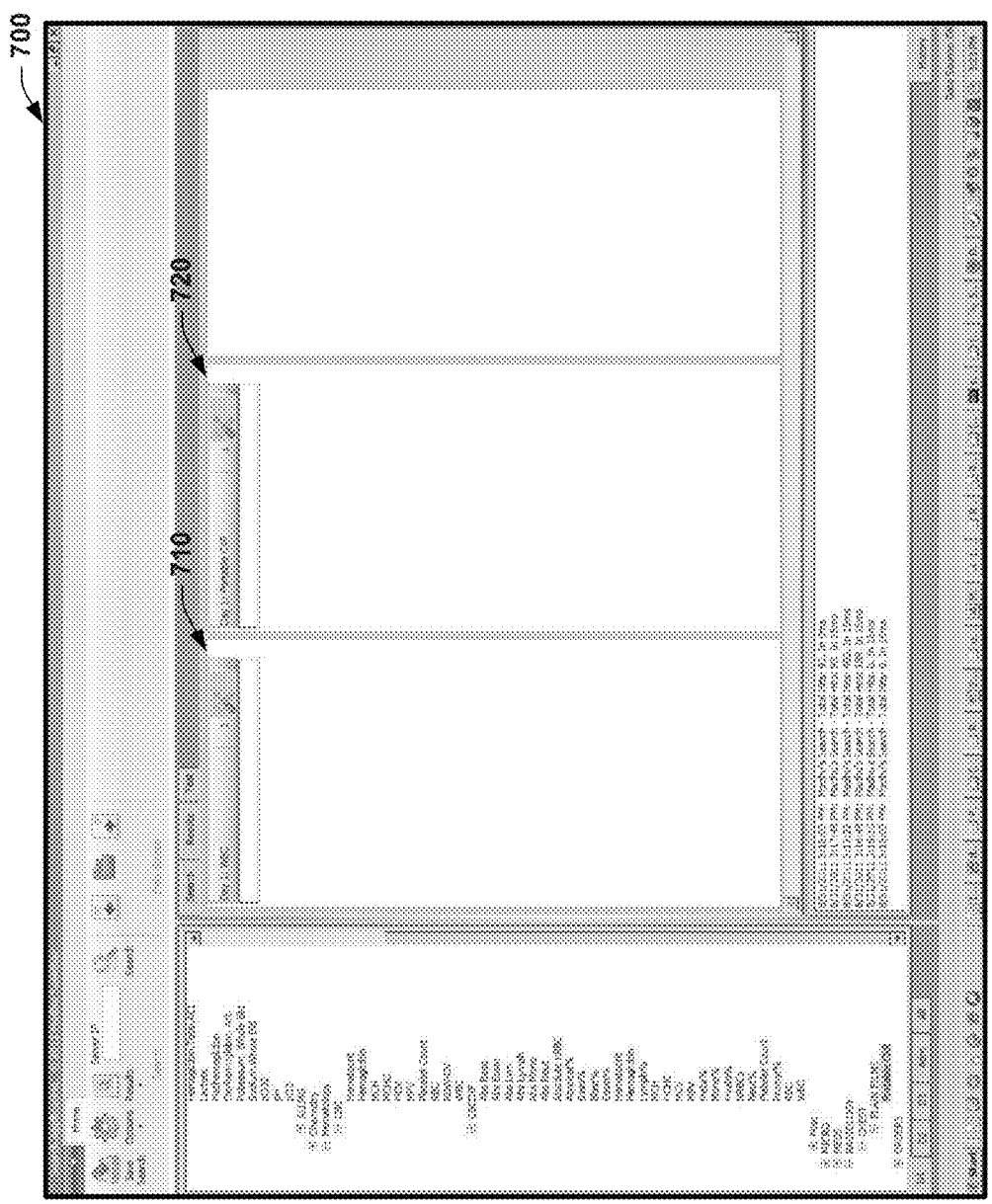
FIG. 7 illustrates another example of a graphical user interface that can implement searching.

FIG. 7 illustrates an example interface 700 demonstrating multiple search palettes 710 and 720 can be opened concurrently to facilitate searching of clinical information. As one example, the query terms within a given palette can be ORed together and the query terms in the different respective palettes can be ANDed together to create a corresponding combined query. In other examples, different Boolean logic, mathematical expressions and combinatorial logic can be utilized to form search expressions for querying the inverted index documents generated based on this disclosure. In the example of FIG. 7, a day 1 white blood cell (WBC) search event can initiated via palette 710 (e.g., same as FIG. 6) and a day 1 portable chest x-ray (CXR) search event can be implemented in the other search palette 720, such that the aggregate search is the ANDing of the two searches. As can be appreciated, a plurality of such search palettes can be initiated as to provide corresponding search palettes.

Figure 8:
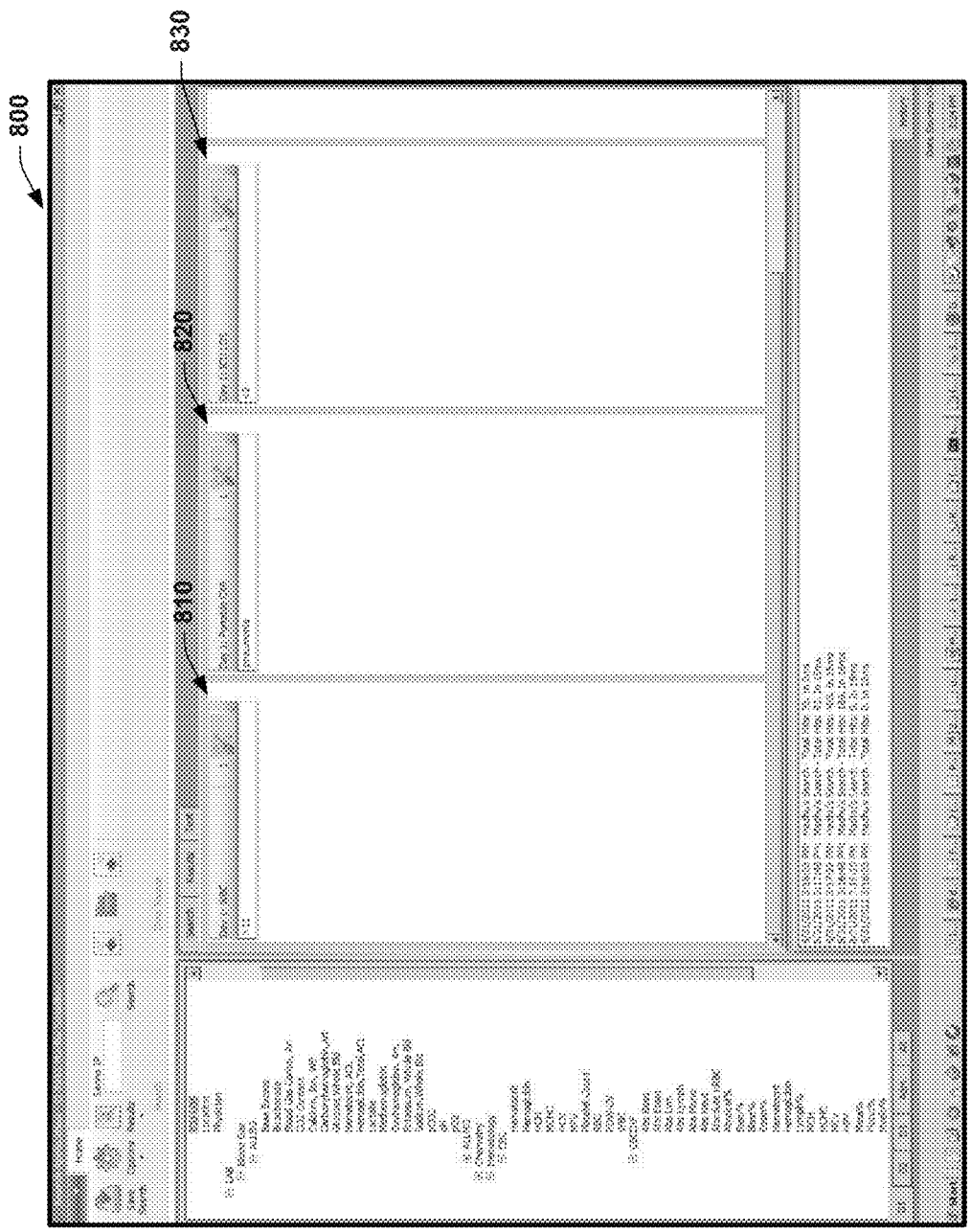
FIG. 8 illustrates yet another example of a graphical user interface that can implement searching.

An example of a three palette search interface is shown in the GUI 800 of FIG. 8. The GUI 800 includes a WBC search palette is opened at 810, a portable CXR search palette at 820, and a length of stay (LOS) in the ICU search palette is opened at 830. In this example, a search term of ">11" is invoked for the WBC search palette 810, "pneumonia" is employed as the search term for the Portable CXR search palette 820, and "<2" is the term employed for the ICU LOS search palette at 830. As can be appreciated, a plurality of different search terms can be employed including mathematical expressions (e.g., +, −, >, <, and so forth), logical expressions (e.g., and, or, not, and so forth), and other clinical terms of interest.

Figure 9:
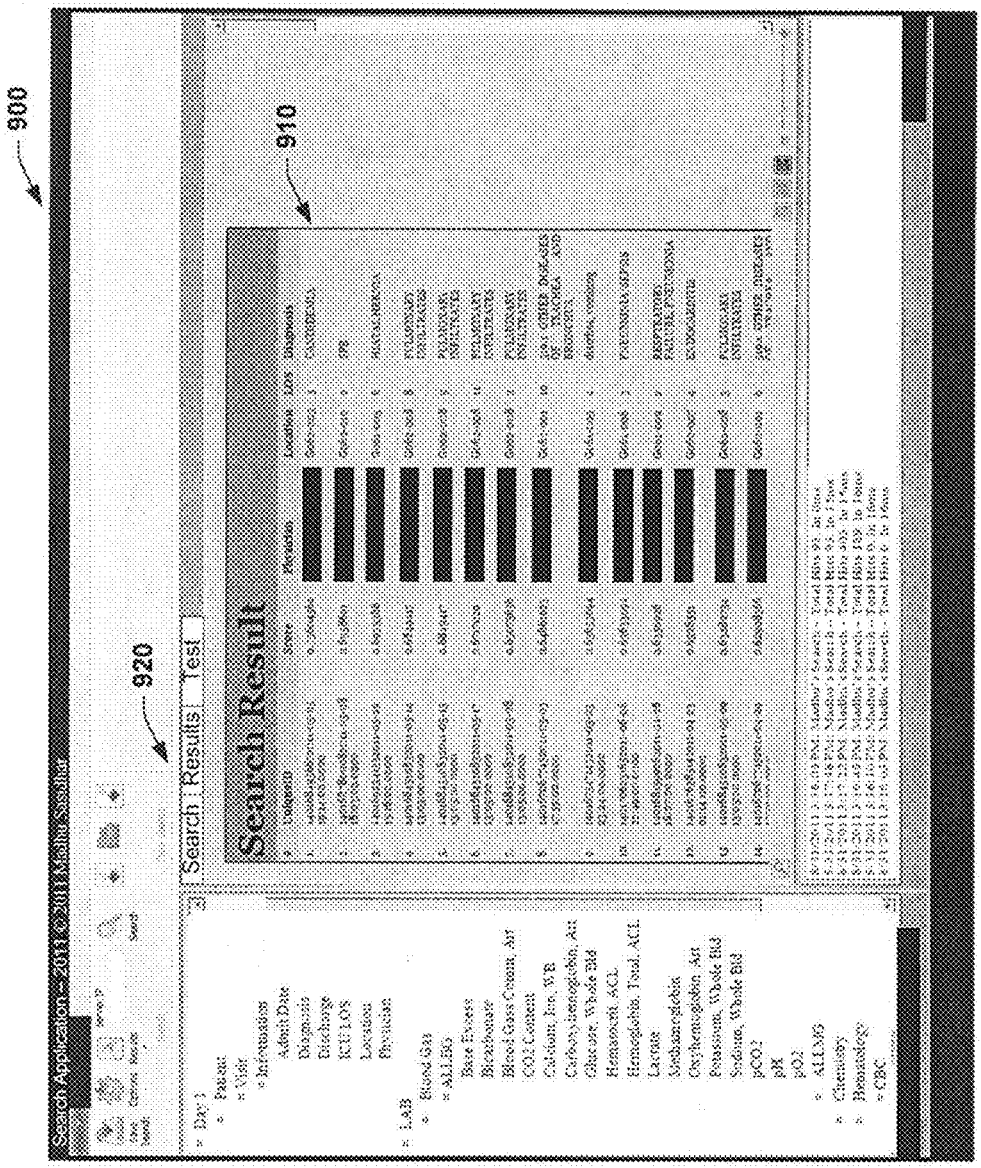
FIG. 9 illustrates example of a graphical user interface that demonstrating search results that can be retrieved in response to a search provided via the GUI of FIG. 8.

FIG. 9 demonstrates an example of an interface 900 demonstrate search results, such as in response to the search shown in FIG. 8. FIG. 6 shows a ranked results pane 910. Results for a given search term can be shown and can be selected via button 920. As shown, the results at 910 can be ranked from most relevant at the top (e.g., result having highest computed score) to the result having the lowest score at the bottom of the results list. Such scoring can be computed based on term frequency, inverse frequency and/ or weighting applied to terms. For instance, the more search terms that match an entry in the index document can produce a higher the score. The results pane 910 can include a unique document identifier (e.g., for the inverted index document), the score, location, length of stay, physician and diagnosis, which can facilitate inquiry into the returned results.

Figure 10:
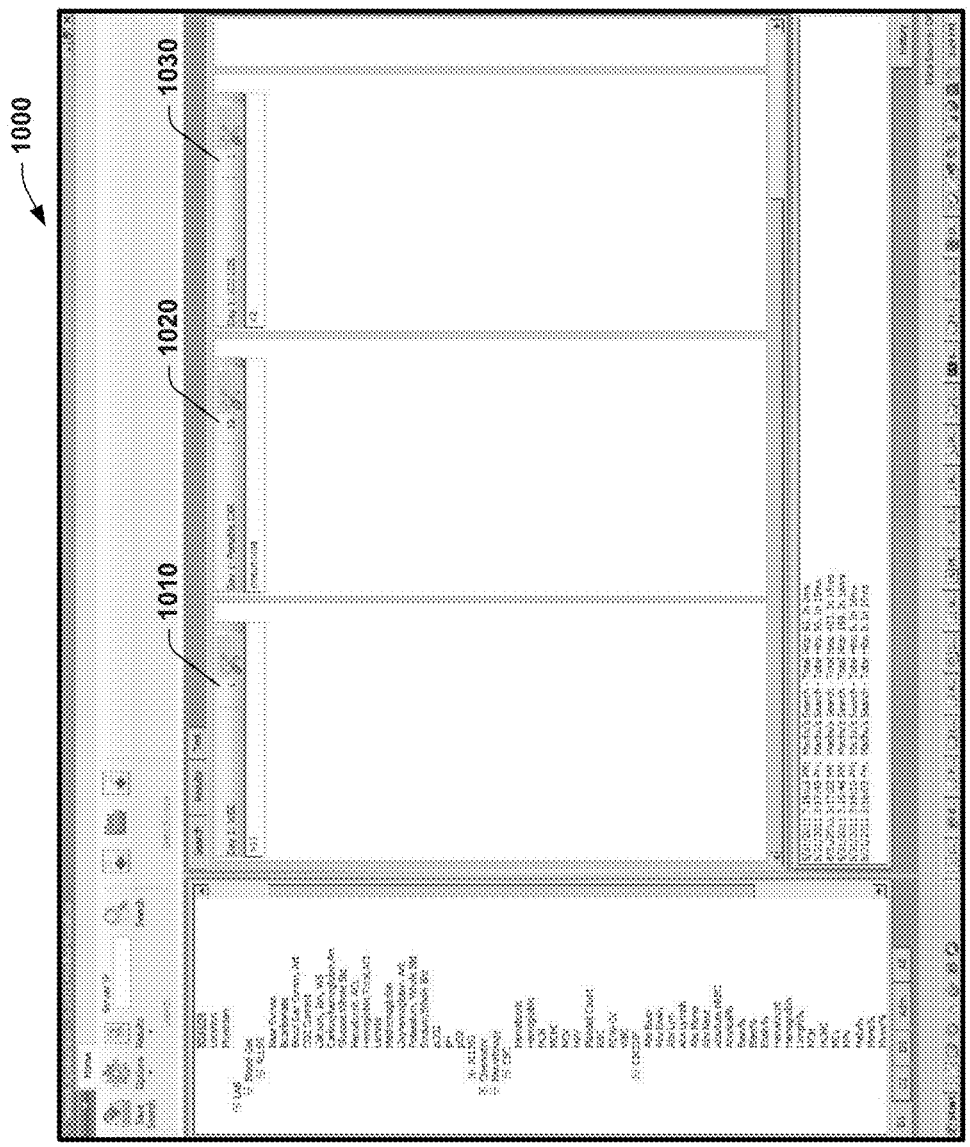
FIG. 10 illustrates an example of a graphical user interface that can implement searching with weighting.
Figure 11:
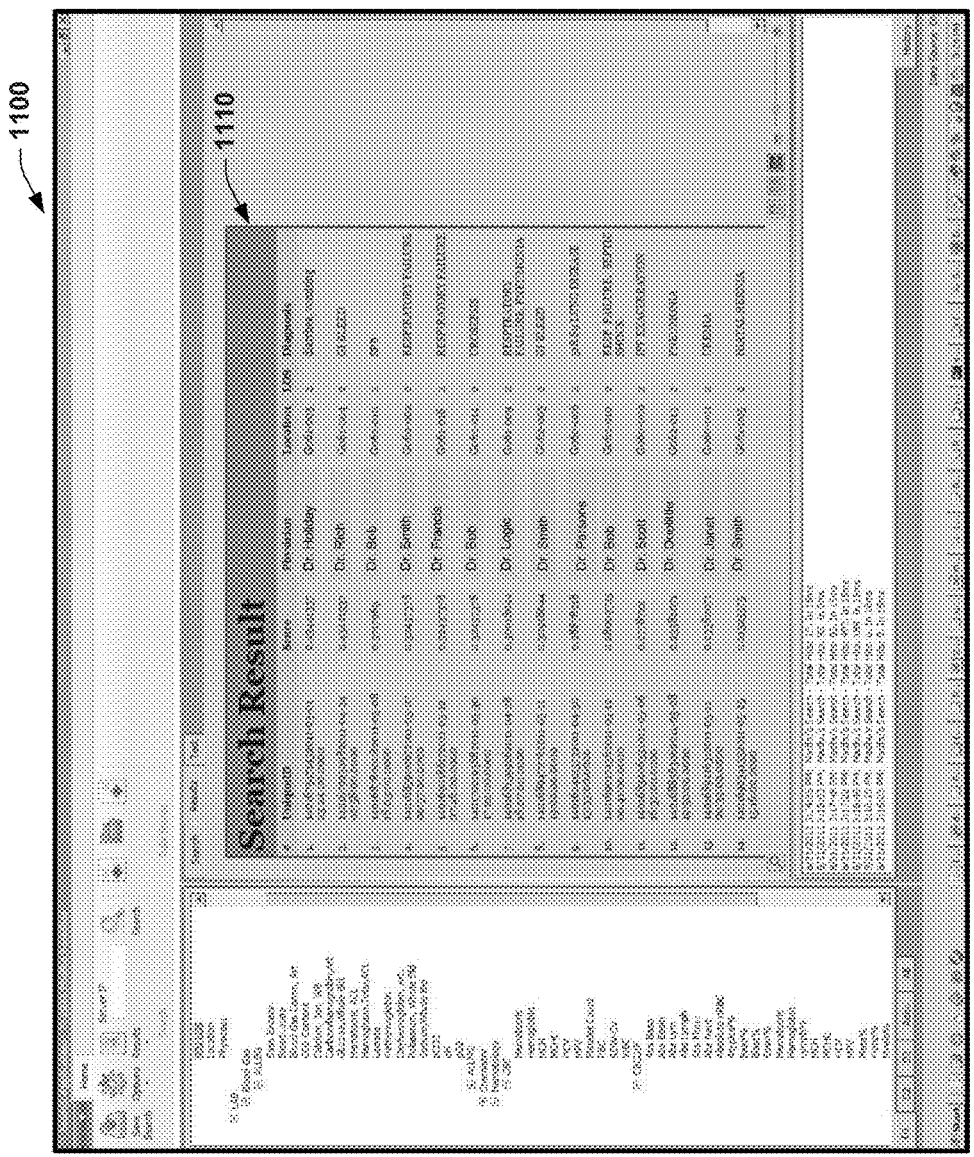
FIG. 11 illustrates example of a graphical user interface that demonstrating search results that can be retrieved in response to a search provided via the GUI of FIG. 10.

FIGS. 10 and 11 illustrate other similar examples for searching and for displaying clinical information and ranked results. In the examples of FIGS. 10 and 11, the search includes the same search terms as in the examples of FIG. 8, but a different weighting of the search terms is provided via weighting GUI elements (e.g., input boxes) 1010, 1020 and 1030. It is to be appreciated that results returned for the same search terms and search values will be the same; however, different weighting of search terms results in a different ordering of the results set. Thus, a user can change weighting selectively in response to a user input via the GUI to see the impact of increasing an importance of one or more search terms (in substantially real time). In the example of FIG. 10, the search palette 1020 for a portable CXR includes a weighting of 12 (compared to a weighting of 1 in FIG. 8). FIG. 11 thus demonstrates a GUI 1100 with search results 1110 organized in an order based on the modified weighting of search terms shown in FIG. 10.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A computer-implemented method, comprising:
   acquiring data from at least one data source, the acquired data including health data comprising a plurality of data objects for at least one patient, the at least one data source comprises at least one of an electronic health record repository, a laboratory information systems, or an analytic systems;
   transforming, by a processor, the acquired data into episode model data according to a context-specific data model and storing the episode model data in a database;

generating, by a processor, at least one inverted index document for at least a portion of an episode for the patient by a processor based on the episode model data, the generating comprising:
- analyzing selected data objects in the episode model data;
- determining a respective qualified name for selected data objects in the episode model data according to the context-specific data model, wherein the respective qualified name comprises at least two of a temporal identifier, a field name, and a data type; and
- adding the respective qualified name to each of the selected data objects in the inverted index document;

searching, by a processor, the at least one inverted index document by a processor based on a query that includes at least a portion of a corresponding qualified name; and storing, in memory, results data that includes search results in response to the searching.

2. The method of claim 1, wherein the at least one inverted index is generated at a scheduled time interval.

3. The method of claim 1, wherein the searching further comprising executing one or more queries periodically at a predetermined time interval or in response to an event trigger.

4. The method of claim 3, further comprising
evaluating the results data; and
providing an alert based on the evaluation indicating the occurrence of a predetermined alert condition.

5. The method of claim 1, wherein the transforming further comprises:
- segmenting the acquired data into temporal segments of the episode relative to a predefined base time, each of the temporal segments spanning a time period; and
- adding the temporal identifier to selected data objects in each inverted index document to indicate which of the temporal segments each of the selected data objects belongs.

6. The method of claim 5, wherein the temporal identifier comprises a temporal prefix of a qualified name that is pre-pended to each of the selected data objects, according to a predefined schema, to identify a time segment for the selected data objects relative to a time when the inverted index document is generated.

7. The method of claim 1, wherein the temporal identifier specifies one of a plurality of time segments for the episode of care in which each of the selected data objects has been determined to reside, the field name provides a descriptor to represent information content for each of the selected data objects, and the data type indicates a predefined characteristic for data values stored in each of the selected data objects.

8. The method of claim 1, wherein the generating at least one inverted index document further comprises removing stop words from predetermined types of data objects in the episode model data and semantically expanding the predetermined types of the data objects in the episode model data to provide modified versions thereof in the inverted index document.

9. The method of claim 1, further comprising:
- computing, by a processor, a score for the search results in the results data, and
- ranking, by a processor, the search results in an order based on the computed score for each of the search results.

10. The method of claim 9, wherein the query comprises a plurality of search terms selected according to the data model, the method further comprising assigning a relative weight to each of the plurality of search terms such that the order of the search results varies depending on the relative weighting of the search terms.

11. The method of claim 10, wherein the relative weight is assigned in response to a user input.

12. The method of claim 1, wherein the at least one data source comprises an electronic health record repository.

13. A non-transitory machine readable medium having instructions executable by a processing resource, the instructions comprising:
- a data converter programmed to access health data comprising a plurality of data objects from at least one data source and transform the accessed data to episode data for a given patient based on a data model that defines at least one of structure and content for storing the episode data in a database for an episode of care for the given patient, the at least one data source comprising one or more of an electronic health record repository, a laboratory information system, or an analytic system; and
- an index generator programmed to:
  - generate an inverted index document based on the episode data;
  - analyze selected data objects in the episode model data;
  - determine a name for each of a plurality of selected data objects in the episode data according to the data model, wherein the name comprises at least two of a temporal identifier, a field name, and a data type; and
  - add the name to each of the plurality of selected data objects in the inverted index document;
- a search engine programmed to:
  - query the inverted index document to search the at least one inverted index document, the query comprising at least one search term corresponding to at least a portion of the name associated with at least one of the plurality of selected data objects; and
  - provide search results in response to query.

14. The medium of claim 13, wherein the data converter is programmed to determine the name that is assigned to each of the plurality of data objects as a qualified name, the qualified name being added to each of the selected data objects in the inverted index document according to a schema.

15. The medium of claim 14, wherein the data converter further comprises:
- a temporal segmenting function to segment the accessed data into time segments relative to an event; and
- a prefix generator to generate a temporal prefix, corresponding to a portion of the qualified name, to specify one of the time segments for each of the selected data objects, wherein the temporal identifier comprises the temporal prefix.

16. The medium of claim 15, wherein the event is a time when the inverted index document is generated.

17. The medium of claim 13, wherein the search engine is programmed to execute one or more queries periodically at a predetermined time interval or in response to an event trigger.

18. The medium of claim 13, further comprising an alert generator to evaluate the results data and provide an alert based on the evaluation indicating the occurrence of a predetermined alert condition.

19. The medium of claim 13, wherein the index generator further comprises a semantic expansion function to expand to include an expanded set of values in the inverted index document that is generated, and a stop word removal function to remove predetermined stop words from of data objects that store a predetermined type of data in the database such that the predetermined stop words are omitted from the inverted index document that is generated.

20. A non-transitory machine readable medium having instructions executable by a processing resource, the instructions comprising:
a data converter programmed to:
  access health data comprising a plurality of data objects from at least one data source and transform the accessed data to episode data for a given patient based on a data model that defines at least one of structure and content for storing the episode data in a database for an episode of care for the given patient, the at least one data source comprising one or more of an electronic health record repository, a laboratory information system, or an analytic system;
  determine a field name for each selected data object according to the data model; and
  determine a data type for each selected data object according to the data model,
an index generator programmed to:
  generate an inverted index document based on the episode data;
  analyze each selected data object in the episode model data;
  determine a name for each selected data object in the episode data according to the data model; and
  add name to each selected data object in the inverted index document based on a temporal prefix, the field name and the data type determined for each respective data object, wherein the temporal prefix specifies a respective time segment for each selected data object; and
a search engine programmed to:
  query the inverted index document to search the at least one inverted index document, the query comprising at least one search term corresponding to at least a portion of the name associated with at least one selected data object; and
  provide search results in response to query.

* * * * *